United States Patent
Abhari et al.

(10) Patent No.: US 10,593,052 B2
(45) Date of Patent: Mar. 17, 2020

(54) METHODS AND SYSTEMS FOR UPDATING AN EXISTING LANDMARK REGISTRATION

(71) Applicants: Kamyar Abhari, Toronto (CA); Neil Jeffrey Witcomb, Toronto (CA); Stewart David McLachlin, Toronto (CA); Kai Michael Hynna, Toronto (CA); Gal Sela, Toronto (CA)

(72) Inventors: Kamyar Abhari, Toronto (CA); Neil Jeffrey Witcomb, Toronto (CA); Stewart David McLachlin, Toronto (CA); Kai Michael Hynna, Toronto (CA); Gal Sela, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 0 days.

(21) Appl. No.: 15/684,433

(22) Filed: Aug. 23, 2017

(65) Prior Publication Data

US 2019/0066314 A1 Feb. 28, 2019

(51) Int. Cl.
*G06T 7/33* (2017.01)
*A61B 34/20* (2016.01)
(Continued)

(52) U.S. Cl.
CPC .............. *G06T 7/337* (2017.01); *A61B 17/86* (2013.01); *A61B 34/20* (2016.02); *A61B 90/361* (2016.02);
(Continued)

(58) Field of Classification Search
CPC combination set(s) only.
See application file for complete search history.

(56) References Cited

U.S. PATENT DOCUMENTS

| 5,429,135 A | 7/1995 | Hawman et al. |
| 7,831,096 B2 * | 11/2010 | Williamson, Jr. ...... G06T 15/00 382/195 |

(Continued)

FOREIGN PATENT DOCUMENTS

WO 1993/18470 A1 9/1993

OTHER PUBLICATIONS

Search report issued by the Intellectual Property Office of the United Kingdom in relation to corresponding GB Application No. GB1813210.0 dated Feb. 13, 2019, 5 pgs.

(Continued)

*Primary Examiner* — Tsung Yin Tsai
(74) *Attorney, Agent, or Firm* — Rowand LLP

(57) ABSTRACT

Methods and image-guided surgical navigation systems for updating an existing landmark registration of one or more landmark features in a common coordinate space are provided. The image-guided surgical navigation system includes a processor, an imaging device coupled to the processor, and a memory coupled to the processor. The image-guided surgical navigation system may be configured to capture a planar image of a region of interest, where the planar view image includes illustration of the one or more landmark features; generate a depth map from the planar view image; based on the depth map, identify a current location of the one or more landmark features in the common coordinate space; and transform the existing landmark registration to the current location of the one or more landmark features in the common coordinate space.

15 Claims, 8 Drawing Sheets

(51) Int. Cl.
  *A61B 90/00* (2016.01)
  *G06T 7/50* (2017.01)
  *G06T 7/73* (2017.01)
  *A61B 17/86* (2006.01)
(52) U.S. Cl.
  CPC .................. *G06T 7/33* (2017.01); *G06T 7/50* (2017.01); *G06T 7/73* (2017.01); *A61B 2034/2055* (2016.02); *A61B 2034/2065* (2016.02); *A61B 2034/2068* (2016.02); *A61B 2090/363* (2016.02); *A61B 2090/365* (2016.02); *A61B 2090/367* (2016.02); *A61B 2090/373* (2016.02); *A61B 2090/374* (2016.02); *A61B 2090/378* (2016.02); *A61B 2090/3735* (2016.02); *A61B 2090/3762* (2016.02); *A61B 2090/3937* (2016.02); *A61B 2576/00* (2013.01); *G06T 2200/04* (2013.01); *G06T 2207/10012* (2013.01); *G06T 2207/30004* (2013.01); *G06T 2207/30204* (2013.01)

(56) References Cited

U.S. PATENT DOCUMENTS

| | | | | |
|---|---|---|---|---|
| 8,108,072 B2* | 1/2012 | Zhao | ............ | G06K 9/3216 382/153 |
| 8,131,031 B2* | 3/2012 | Lloyd | ............ | A61B 5/06 382/128 |
| 8,147,503 B2* | 4/2012 | Zhao | ............ | G06K 9/3241 382/128 |
| 9,119,670 B2* | 9/2015 | Yang | ............ | A61B 5/055 |
| 2005/0215879 A1* | 9/2005 | Chuanggui | ............ | G06T 7/001 600/407 |
| 2007/0238947 A1 | 10/2007 | Pescatore et al. | | |
| 2008/0119725 A1* | 5/2008 | Lloyd | ............ | A61B 90/36 600/424 |
| 2009/0088897 A1* | 4/2009 | Zhao | ............ | G06K 9/3216 700/250 |
| 2011/0158488 A1* | 6/2011 | Cohen | ............ | A61B 34/20 600/476 |
| 2012/0215108 A1 | 8/2012 | Park et al. | | |
| 2013/0060146 A1* | 3/2013 | Yang | ............ | A61B 5/055 600/476 |
| 2015/0265369 A1* | 9/2015 | Garbey | ............ | A61B 5/061 600/410 |
| 2016/0000515 A1* | 1/2016 | Sela | ............ | G06T 7/337 600/424 |
| 2016/0019716 A1 | 1/2016 | Huang et al. | | |
| 2017/0366773 A1* | 12/2017 | Kiraly | ............ | H04N 5/372 |
| 2018/0035966 A1 | 2/2018 | Merlet et al. | | |

OTHER PUBLICATIONS

Canadian Office Action dated May 22, 2019, Application No. 3,013,128.

* cited by examiner

METHODS AND SYSTEMS FOR UPDATING AN EXISTING LANDMARK REGISTRATION

FIELD

The present application generally relates to image-guided surgical navigation systems and, in particular, to updating an existing landmark registration by image-guided surgical navigation systems.

BACKGROUND

During an image-guided medical procedure, an image-guided surgical navigation system may correlate a position of a previously acquired patient image with a physical position of the patient. To facilitate the correlation, surgical navigation systems may rely upon optical tracking of landmark features of the patient's anatomy or may rely upon reference markers affixed to the patient's anatomy for integrating the patient image with the patient position into a common coordinate space.

The common coordinate space may be formed by amalgamating a virtual coordinate space and an actual coordinate space. The virtual coordinate space may be defined as a coordinate space in which virtual representation of objects exist. The actual coordinate space may be defined as the space where actual objects, such as the patients or surgical instruments, exist. Thus, correlation of the patient image with the physical position of the patient is accomplished through the process of registration. Ensuring accuracy of registration is desirable and necessary for maintaining confidence of the information presented to the medical professional during the image-guided medical procedure.

BRIEF SUMMARY

In one aspect, the present application describes a method of updating existing landmark registration features in a common coordinate space of an image-guided surgical navigation system. The method includes capturing a planar view image of a region of interest, the planar view image including illustration of the one or more landmark features; generating a depth map from the planar view image; based on the depth map, identifying a current location of the one or more landmark features in the common coordinate space; and transforming the existing landmark registration to the current location of the one or more landmark features in the common coordinate space.

In another aspect, the present application describes an image-guided surgical navigation system. The image-guided surgical navigation system includes a processor; an imaging device coupled to the processor; and a memory coupled to the processor and storing processor-readable instructions. When executed, the instructions cause the processor to capture a planar view image of a region of interest, the planar view image including illumination of the one or more landmark features; generate a depth map from the planar view image; based on the depth map, identify a current location of the one or more landmark features in a common coordinate space; and transform the existing landmark registration to the current location of the one or more landmark features in the common coordinate space.

In another aspect, the present application describes non-transitory computer-readable medium storing processor-readable instructions which, when executed, configure a processor to perform one or more of the operations described herein. In this respect, the term processor is intended to include all types of processing circuits or chips capable of executing program instructions.

Other aspects and features of the present application will be understood by those of ordinary skill in the art from a review of the following description of examples in conjunction with the accompanying figures.

BRIEF DESCRIPTION OF THE DRAWINGS

Reference will now be made, by way of example, to the accompanying drawings which show example embodiments of the present application.

Similar reference numerals may have been used in different figures to denote similar components.

DESCRIPTION OF EXAMPLE EMBODIMENTS

Figure 1:
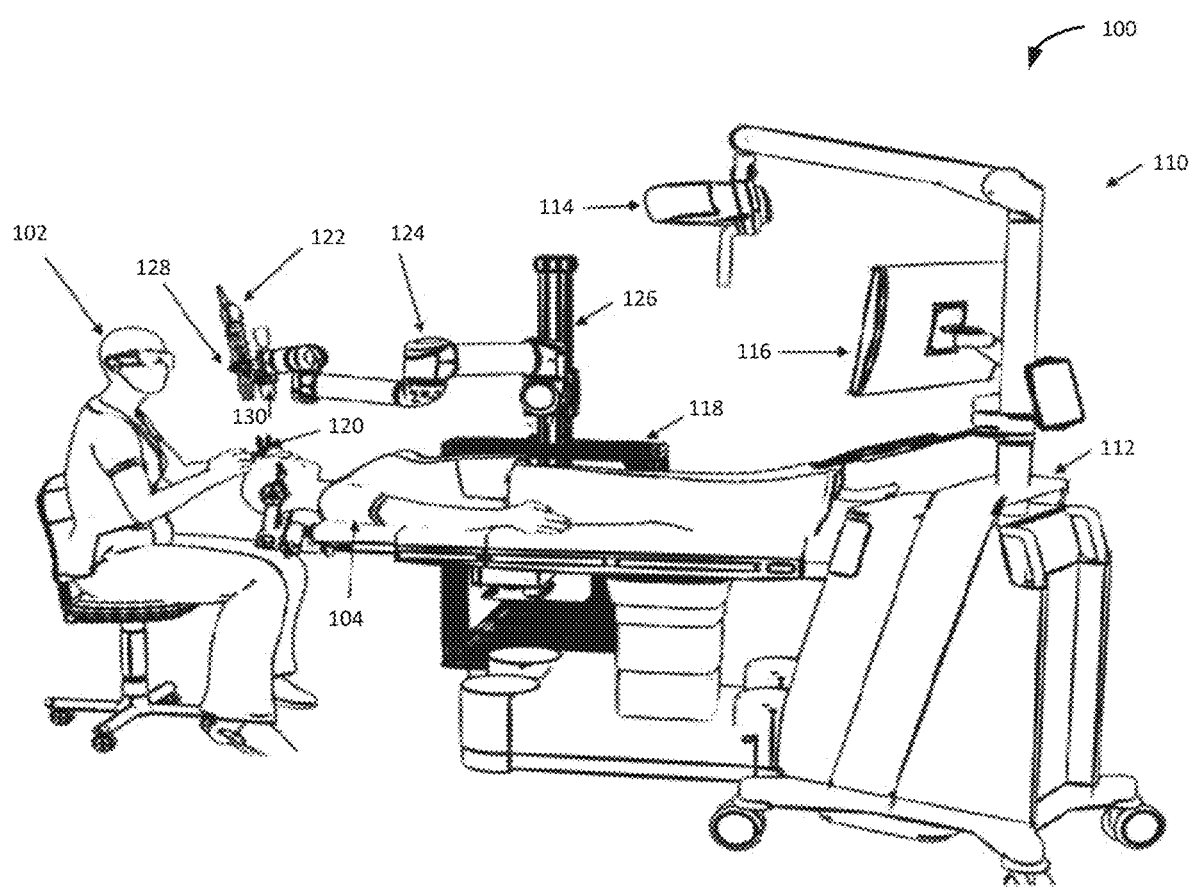
FIG. 1 illustrates an operating room environment having an image-guided surgical navigation system, in accordance with an embodiment of the present application.

Various examples and aspects of the present application will be described with reference to the details discussed below. The following description and drawings are illustrative of the present application and are not to be construed as limiting the present application. Numerous details are described to provide a thorough understanding of various embodiments. However, in certain instances, well-known or conventional details are not described in order to provide a concise discussion of the embodiments of the present application.

As used herein, the terms "comprises" and "comprising" are to be construed as being inclusive and open ended, and not exclusive. Specifically, when used in the specification and claims, the terms "comprises" and "comprising" and variations thereof mean the specified features, steps, or components are included. These terms are not to be interpreted to exclude the presence of other features, steps, or components.

As used herein, the term "exemplary" means "serving as an example, instance, or illustration", and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In a non-limiting example, the terms "about", "approximately", and "substantially" may mean plus or minus 10 percent or less.

As used herein, the phrase "intraoperative" refers to an action, process, method, event or step that occurs or is carried out during at least a portion of a medical procedure. Intraoperative, as defined herein, is not limited to surgical procedures, and may refer to other types of medical procedures.

In the present application, the term "and/or" is intended to cover all possible combination and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

During an image-guided medical procedure, an image-guided surgical navigation system may correlate a position of a previously acquired patient image (e.g., preoperative image) with an intraoperative position of the patient. To facilitate the correlation, the image-guided surgical navigation system may rely upon optical tracking of landmark features of the patient's anatomy or may rely upon reference markers, such as fiducial markers, affixed to the patient's anatomy. The correlation of the patient image with the intraoperative position of the patient may be accomplished through the process of registration.

The term "registration" or "image registration" refers to the process of determining the transform to be used in correlating points across different coordinate spaces. Registration correlates different coordinate spaces so that data positioned in one coordinate space may be mapped to the other coordinate space using the transform. Data may include photographs, data from different sensors, times, depths, or viewpoints. The process of registration may be used in some examples for medical imaging in which images from different imaging modalities are co-registered. Registration may be used to compare or integrate data obtained from the different modalities for presentation on a common platform or display.

The present application is generally directed to updating an existing landmark registration by image-guided surgical navigation systems. In an example surgical procedure, such as a craniotomy, where identifiable features may be created on the patient's anatomy as part of a process (e.g., a craniotomy opening), intraoperatively acquired image and scan data may be used to identify relative change in position of a part of the patient's body with respect to landmark features or reference markers. A spatial transform may be derived from the identified change in position, and the transform may be used to obtain an updated landmark registration.

As will be described herein, intraoperatively acquired images may already be captured during a medical procedure workflow. The intraoperatively acquired images may be used during operations for updating an existing landmark registration. Accordingly, it may not be necessary to undertake other preoperative setup steps, such as actively setting recovery points (e.g., drilling of recovery points on a patient's skull) prior to the medical procedure, which may be an added procedural step that may suffer from inconsistency and variability depending on the medical processional performing the added procedural step.

It will be understood that there may be numerous registration techniques available and one or more techniques may be applied to aspects of the present application. Non-limiting examples may include intensity-based methods that compare intensity patterns in images via correlation metrics, while feature-based methods may find correspondence between image features, such as points, lines, and contours. Registration methods may also be classified according to the transformation models used to relate an actual coordinate space to a virtual coordinate space.

In some examples, single-modality methods may be distinguished from multi-modality methods. Single-modality methods may register images in the same modality acquired by the same scanner or sensor type. For example, a series of magnetic resonance (MR) images may be co-registered. Multi-modality methods may be used to register images acquired by different scanner or sensor types. For example, multi-modality methods may be used to register images from magnetic resonance imaging (MRI) and positron emission tomography (PET). In some other examples, multi-modality registration methods may be used for imaging of a patient's head and/or brain, where images may frequently be captured using different imaging devices or technologies. Examples may include registration of brain computerized tomography (CT) and MRI images, or PET and CT images for tumor localization. Other examples may include registration of contrast-enhanced CT images with non-contrast-enhanced CT images, or registration of ultrasound images with CT images.

Reference is now made to FIG. 1, which illustrates an operating room environment 100 having an image-guided surgical navigation system 110, in accordance with an embodiment of the present application. A medical professional 102, such as a surgeon, may conduct a surgical procedure on a patient 104 in the operating room environment 100 with assistance of the image-guided surgical navigation system 110.

The image-guided surgical navigation system 110 may include an equipment tower 112, a tracking detector 114, a display 116, a positioning system 118, and fiducial markers 120. The fiducial markers 120 may be affixed to the patient 104 or parts of the patient 104 or to objects within the operating room environment 100. In FIG. 1, the illustrated fiducial markers 120 are positioned for use during a port-based surgical procedure. For example, the fiducial markers 120 may be positioned to assist the medical professional 102 with image-guided tumor resection. It will be understood that the fiducial markers 120 may be positioned at any other location within the operating room environment 100 or affixed to any part of the patient 104, such that the image-guided surgical navigation system 110 may track objects.

The tracking detector 114 may include an optical tracking device, such as a tracking camera, a video camera, a three-dimensional scanner, or any other suitable imaging device for detecting the fiducial markers 120 or other landmark features. For example, landmark features may be fiducial markers 120. Landmark features may also be uniquely identifiable features of the patient's anatomy. In other examples, landmark features may also be derived from identifiable contours of objects being tracked by the image-guided surgical navigation system 110.

As described, in FIG. 1, the medical professional 102 may be performing a tumor resection on the patient 104 and may be utilizing an imaging device 122 (e.g., a scope and/or camera) for magnifying the area of interest when performing the tumor resection. For example, the imaging device 122 may be a microscope for magnifying an area of tissue that the medical professional 102 may be operating on. The imaging device 122 may be an external microscope, a video scope, wide field camera, or any other image capturing device for assisting the medical professional 102 in viewing tissues and instruments within a desired area of interest. Images captured by the imaging device 122 may be displayed on the display 116, such that the medical professional 102 may navigate instruments through tissues in the area of interest. In some examples, the imaging device 122 may capture intraoperative images of a region of interest, where the intraoperative images may be displayed on the display 116, may be correlated with preoperative images, or may be used for updating an existing landmark registration of one or more landmark features in a common coordinate space.

The positioning system 118 may include an arm 124, a lifting column 126, and an end effector 128. The lifting column 126 may be connected to a frame of the positioning system 118, and the proximal end of the arm 124 may be connected to the lifting column 126.

In some other embodiments, the arm 124 may be coupled to a horizontal beam, which may be connected to the lifting column 126 or to the frame of the positioning system 118. The arm 124 may include multiple joints for providing multiple degrees of freedom, such as 5, 6, or 7 degrees of freedom.

The end effector 128 may be attached to a distal end of the arm 124. The end effector 128 may accommodate a plurality of instruments or tools that may assist the medical professional 102 with medical procedures. In FIG. 1, the end effector 128 may be securing an external scope and camera. However, in some embodiments, the end effector 128 may be configured with a wide field camera, microscope and Optical Coherence Tomography (OCT) device, video camera, three-dimensional scanner, or other imaging instruments. In other examples, multiple end effector 128 devices may be coupled to the distal end of the arm 124, such that the medical professional 102 may switch among multiple modalities or devices. For example, the medical professional 102 may need to move between microscope and OCT with stand-off optics. In another example, the medical professional 102 may need to also utilize a precise, smaller range end effector, such as a laser-based ablation system with micro-control.

In some embodiments, the positioning system 118 may receive, as input, spatial position and pose data for the arm 124. The positioning system 118 may also receive, as input, a target region of interest. The target region of interest may be identified by the tracking detector 114 based on fiducial markers 120 affixed to the region of interest. For example, the region of interest may be a portion of the patient 104 where a tumor resection may be required, and where one or more fiducial markers 120 may be affixed.

In some examples, fiducial markers 120 may be affixed to the arm 124, the end effector 128, or other objects within the operating room environment 100, such that the tracking detector 114 may identify the positioning of the arm 124, the end effector 128, or the other objects within the operating room environment 100.

In some examples, a wide-field camera 130 may be coupled adjacent the imaging device 122, such that the wide-field camera 130 and the imaging device 122 may be positioned by the end effector 128. Although the imaging device 122 and the wide-field camera 130 are illustrated as being positioned adjacent one another for simultaneous operation, in some embodiments, the imaging device 122 and the wide-field camera 130 may be utilized independently of the other.

In some examples, the positioning system 118 may be configured for a target or desired position, such that the arm 124 may maneuver the end effector 128 to a spatial position and pose adjacent the region of interest (e.g., for operation during a tumor resection procedure). In some examples, the positioning system 118 may include a foot pedal configured to allow the medical professional 102 to adjust the positioning of the end effector 128 adjacent the region of interest.

Figure 2:
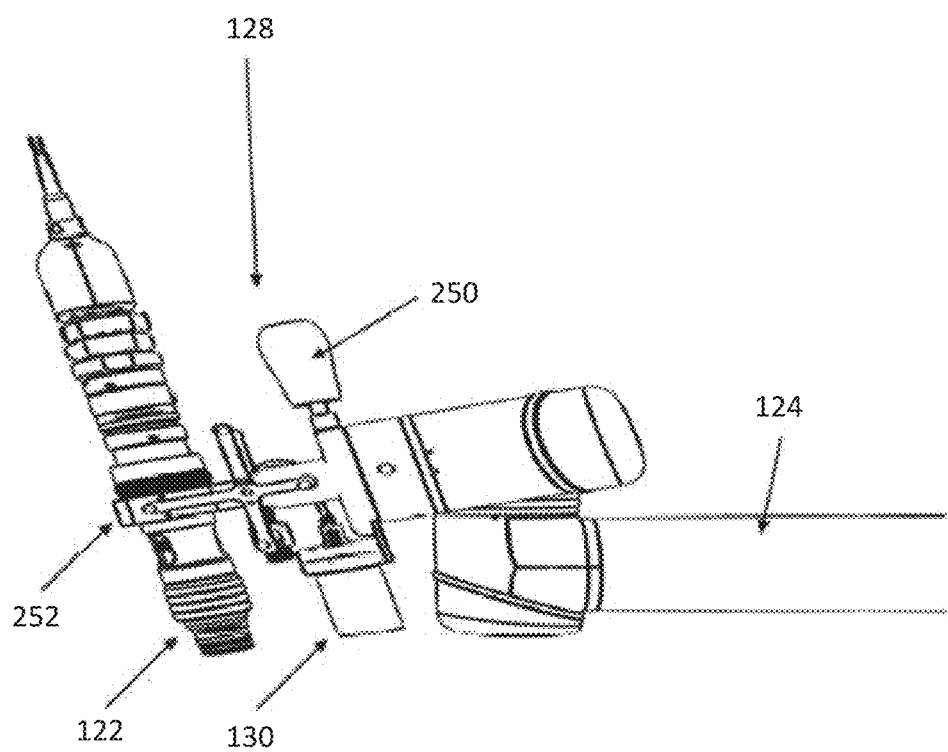
FIG. 2 illustrates an end effector of FIG. 1, in accordance with an embodiment of the present application.

Reference is now made to FIG. 2, which illustrates the end effector 128 of FIG. 1, in accordance with an embodiment of the present application. The end effector 128 may be coupled to the arm 124. The end effector 128 may include a handle 250 and a scope clamp 252 for securing the imaging device 122 to the end effector 128. The end effector 128 may also include a wide-field camera 130. In some examples, instead of the wide-field camera 130, other types of imaging devices may be coupled to the end effector 128, such as still cameras, video cameras, or three-dimensional scanners for monitoring patient movement.

Figure 3:
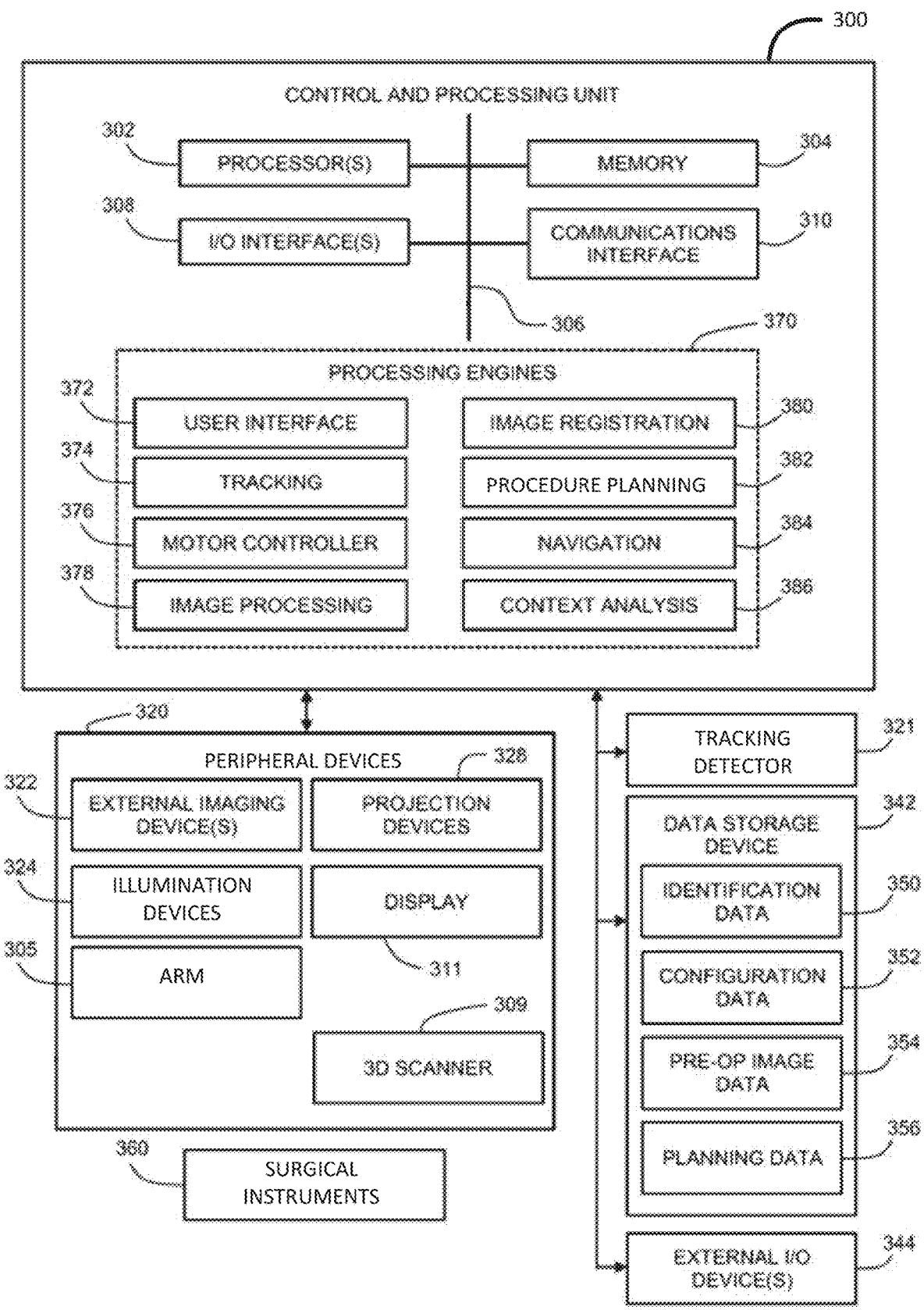
FIG. 3 illustrates a block diagram of the image-guided surgical navigation system of FIG. 1, in accordance with an embodiment of the present application.

Reference is now made to FIG. 3, which illustrates a block diagram of components of the image-guided surgical navigation system 110 of FIG. 1, in accordance with an embodiment of the present application. The image-guided surgical navigation system 110 may include a control and processing unit 300. In some examples, the control and processing unit 300 may be included within the equipment tower 112 (FIG. 1). The control and processing unit 300 may include one or more processors 302, memory 304, a system bus 306, input/output interfaces 308, and a communication interface 310.

The control and processing unit 300 may interface with external devices, including a tracking detector 321, which in some examples may be the tracking detector 114 of FIG. 1. The control and processing unit 300 may also interface with a data storage device 342. The data storage device 342 may include local or remote memory devices, such as hard drives, digital media devices, or server devices, having storage and/or database capabilities therein. As illustrated in FIG. 3, the data storage device 342 may include identification data 350, such as data for identifying surgical instruments 360. The data storage device 342 may also include configuration data 352 for the image-guided surgical navigation system 110 (FIG. 1). The data storage device 342 may also include pre-operative image data 354 and medical procedure planning data 356. Pre-operative image data 354 may include previously acquired patient or preoperative images. As will be described herein, in some examples, the image-guided surgical navigation system 110 may be configured to rely on landmark features, such as fiducial markers, for integrating previously acquired patient images with a current physical position of the patient 104 during a medical procedure. Although the data storage device 342 is illustrated as a collective device in FIG. 3, in some examples, the plurality of types of data illustrated in FIG. 3 may be provided across multiple data storage devices. In some examples, the control and processing unit 300 may also interface with external input/output devices 344.

The control and processing unit 300 may also interface with other peripheral devices 320. Example peripheral devices 320 include external imaging devices 322, illumination devices 324, an arm 305 (which in some examples may be the arm 124 of FIG. 1), projection devices 328, three-dimensional scanner 309, or a display 311. In some examples, the three-dimensional scanner 309 may include preoperative or intraoperative imaging devices, such as computerized tomography (CT), magnetic resonance imaging (MRI), ultrasound, ocular coherence tomography (OCT), or structured light imaging probe devices.

In some embodiments, the control and processing unit 300 may be configured to track surgical instruments 360 based on input from peripheral devices 320 and other external devices. For example, the tracking detector 321 may be configured to detect and acquire data relating to surgical instruments 360 within the operating room environment 100. As described herein, the control and processing unit 300 may be configured to register the detected surgical instruments 360 to reference frames of a common coordinate space. For example, the surgical instruments 360 may include specifically arranged fiducial markers. When the tracking detector 321 detects the specifically arranged fiducial markers, the control and processing unit 300 may register the detected surgical instrument 360 to a reference frame and may determine the position and orientation of that surgical instrument 360 within a common coordinate space. In an example, data associated with the specifically arranged fiducial markers for identifying the surgical instruments 360 may be stored as identification data 350.

Example methods described in the present application include operations that may be implemented, at least in part, through processor-executable instructions stored, for example, in the memory 304 or stored in the data storage device 342, described above. In some examples, the control and processing unit 300 may include processing engines 370. The processing engines 370 may be dedicated processing resources for specified tasks. For example, the processing engines 370 may include a user interface engine 372, a tracking engine 374, a motor control engine 376, an image processing engine 378, an image registration engine 380, a procedure planning engine 382, a navigation engine 384, and a context analysis engine 386. The processing engines 370 may be illustrated as separate processing engines. However, in some examples, the processor 302 may dynamically allocate processing engine resources.

Figure 4A:
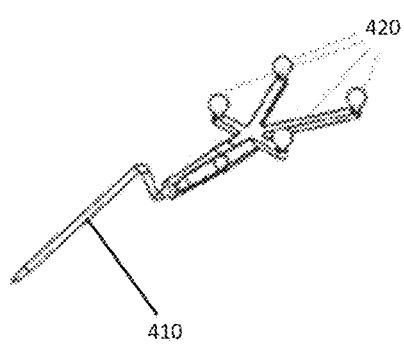
FIGS. 4A and 4B illustrate a surgical instrument and a virtual representation of the surgical instrument, in accordance with an embodiment of the present application.
Figure 4B:
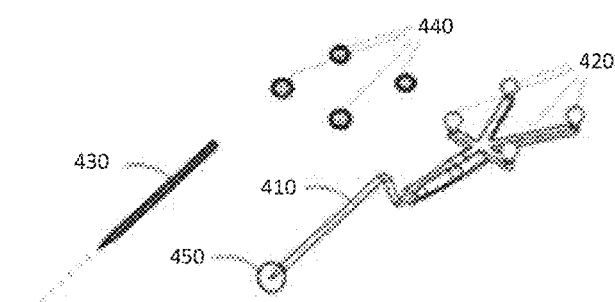

Reference is now made to FIGS. 4A and 4B, which illustrate a surgical instrument 410 that may be locatable by the image-guided surgical navigation system 110 (FIG. 1), in accordance with an embodiment of the present application. In some examples, the surgical instrument 410 illustrated in FIGS. 4A and 4B may be the surgical instrument 360 illustrated in the block diagram of FIG. 3.

The surgical instrument 410 may include a plurality of fiducial markers 420 affixed thereto. The tracking detector 114 (FIG. 1) may detect the plurality of fiducial markers 420 and track the position of the surgical instrument 410. The tracking detector 114 may receive, record, and/or process data regarding the plurality of fiducial markers 420 and associate that data with angle and orientation information. For example, the tracking detector 114 may track, among other items, spatial position of the instrument, including its angle and orientation (i.e., pose). The tracking detector 114 may detect the fiducial markers 420 and may associate the surgical instrument 410 and the detected fiducial markers 420 with a virtual representation. The virtual representation may include a virtual pointer segment 430 and virtual fiducial markers 440, as illustrated in FIG. 4B.

In some embodiments, the fiducial markers 420 or other landmarks may be infrared (IR) reflective spheres configured to be detectable by an IR stereo camera of the tracking detector 114. The surgical instrument 410 may be identifiably associated with a group of fiducial markers 420, which may correspond to a representative volume associated with that surgical instrument 410. The group of fiducial markers 420 may be used to determine the spatial angle and orientation of the volume of the surgical instrument 410 within a common coordinate space. In some examples, three or more fiducial markers 420 may be required to define the spatial angle and orientation of the surgical instrument 410. The Polaris® system available from Northern Digital Inc. is an example of one system that may detect objects or surgical instruments 410 that are associated with four or more fiducial markers 420. Accordingly, surgical instruments 410 or other objects tracked by the tracking detector 114 may be individually identified based on virtual geometric volumes formed by fiducial markers 420. Further, the tracking detector 114 may identify angle and orientation of the tracked surgical instruments 410 based on the identified virtual geometric volumes formed by the fiducial markers 420. In some examples, imaging devices other than the tracking detector 114 may be used for identifying the virtual geometric volumes associated with the fiducial markers 420 or identifying the surgical instruments 410. For example, the imaging device 122 (FIG. 1) may capture intraoperative images during the medical procedure and may be configured to provide data associated with virtual geometric volumes associated with fiducial markers 420.

Referring still to FIG. 4B, the orientation of the fiducial markers 420, or landmark features more generally, may be a proxy for providing information to the image-guided surgical navigation system 110. For example, the orientation of the fiducial markers 420 as detected by the tracking detector 114 may indicate a spatial orientation of the surgical instrument 410, via the spatial orientation of the virtual pointer segment 430. In another example, the orientation of the fiducial markers 420 as detected by the tracking detector 114 may indicate the spatial location of the surgical instrument tip 450, or other information related to the surgical instrument 410.

In some embodiments, fiducial markers 420 or landmarks may utilize radio frequency (RF) technology, electromagnetic (EM) technology, pulsed and un-pulsed light emitting diodes (LEDs), glass spheres, reflective stickers, unique structures and patterns. In some examples, RF and EM fiducial markers may include specific signatures for the tools they may be coupled with. EM and RF fiducial markers may be useful when line-of-sight between the tracking detector 114 and the fiducial markers 420 may not be feasible.

In some examples, an auxiliary camera and/or optical imaging system may detect the three-dimensional fiducial markers. In some examples, the tracking detector 114 may utilize detection of three-dimensional fiducial markers for providing calibration distance information between the tracking detector 114 and the three-dimensional fiducial markers. In some examples the tracking detector 114 may recognize contour of known objects.

As described, during an image-guided medical procedure, the image-guided surgical navigation system 110 (FIG. 1) may correlate a current physical position of the patient with that depicted in a previously acquired patient image. The image-guided surgical navigation system 110 may rely upon landmark features, such as fiducial markers 420, for integrating a position captured in the previously acquired patient image with the current patient position within the operating room environment. Integrating the previously acquired patient image with the current physical position of the patient may be included in a registration process.

Figure 5:
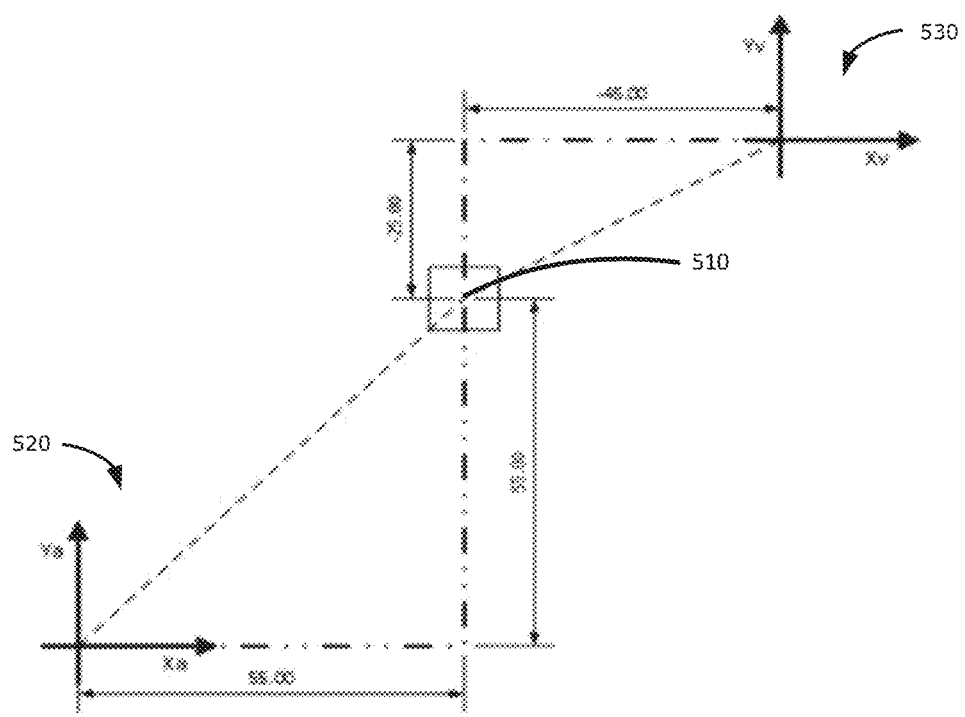
FIG. 5 illustrates a relationship between coordinate spaces for the image-guided surgical navigation system of FIG. 1, in accordance with an embodiment of the present application.

Reference is now made to FIG. 5, which illustrates a relationship between coordinate spaces for the image-guided surgical navigation system 110 of FIG. 1, in accordance with an embodiment of the present application. FIG. 5 illustrates a common coordinate space that may include a common reference coordinate 510. The common coordinate space may be composed of an actual coordinate space 520 and a virtual coordinate space 530. The actual coordinate space 520 may be a coordinate space in which the patient or actual objects may exist. The virtual coordinate space 530 may be a coordinate space in which virtual representations of objects may exist.

As described, the image-guided surgical navigation system 110 may perform registration, which may include determining a transform that may be used to import coordinates from the actual coordinate space 520 of the operating room environment 100 (FIG. 1) to the virtual coordinate space 530. A previously acquired patient image may be associated with a virtual representation in the virtual coordinate space 530. To determine the transform for importing coordinates from the actual coordinate space 520 to the virtual coordinate space 530, the actual coordinate space 520 and the virtual coordinate space 530 may be associated with a common reference coordinate 510.

In FIG. 5, the common reference coordinate 510 is illustrated alongside the actual coordinate space 520 and the virtual coordinate space 530. When the common reference coordinate 510 may be known to the image-guided surgical navigation system 110, the image-guided surgical navigation system 110 may correlate the position of a point in one coordinate space (e.g., actual coordinate space 520 or virtual coordinate space 530) to the other coordinate space (e.g., virtual coordinate space 530 or actual coordinate space 520) by equating the locations of the common reference coordinate 510 in the respective coordinate spaces and solving for unknown translation variables. Translation variables may be used to transform a coordinate of a position in one coordinate space to an equivalent coordinate of the position in the other coordinate space.

The image-guided surgical navigation system 110 may store the position of the common reference coordinate 510 relative to an origin position of the actual coordinate space 520 and an origin position of the virtual coordinate space 530. For example, referring to FIG. 5:

$$(X_{cra}, Y_{cra}) = (55, 55)$$

and $$(X_{crv}, Y_{crv}) = (-45, -25)$$

The subscript "cra" refers to the common reference position relative to the actual coordinate space origin. The subscript "crv" refers to the common reference position relative to the virtual space origin. Utilizing a translation equation describing points $((Y_a, X_a)$ and $(Y_v, X_v))$, where subscript "a" denotes coordinates of a coordinate point relative to the actual coordinate space 520 and the subscript "v" denotes coordinates of a coordinate point relative to the virtual coordinate space 530, the individual coordinate elements from each coordinate space may be equated to solve for translation variables $((Y_T, X_T))$, where the subscript "T" denotes a translation variable:

$$Y_v = Y_a + Y_T$$

$$X_v = X_a + X_T$$

Substituting derived values of points from FIG. 5, the translation variable may be solved. For example:

$$-25 = 55 + Y_T$$

$$-80 = Y_T$$

and $$-45 = 55 + X_T$$

$$-100 = X_T$$

The translation variables may allow a position (e.g., $(Y_a, X_a)$) in the actual coordinate space 520 to be transformed into an equivalent position in the virtual coordinate space 530 using transformation equations provided as follows:

$$X_a = X_v + 100$$

and $$Y_a = Y_v + 80$$

In some examples, the transformation equations may be rearranged to transform a position defined in the virtual coordinate space 530 to the actual coordinate space 520. The above transform variables may allow both virtual and actual objects to be simultaneously defined with respect to the actual coordinate space 520 and the virtual coordinate space 530. Accordingly, when using the transform variables, the actual coordinate space 520 and the virtual coordinate space 530 may be coupled and fiducial markers or landmark features in the actual coordinate space 520 may be registered to fiducial markers or landmark features in the virtual coordinate space 530.

In some embodiments, the common reference coordinate 510 may include a set of points when a surgical instrument or object in the operating room environment 100 (FIG. 1) may be defined with six degrees of movement, such as three spatial degrees of movement commonly referred to as the x, y, and z axis and three rotational degrees of rotation commonly referred to as pitch, yaw, roll. Accordingly, when transforming a position from the actual coordinate space 520 to the virtual coordinate space 530, or vice versa, three or more points may represent the common reference coordinate 510 for capturing the multiple degrees of movement.

Example operations during registration, described above with reference to FIG. 5, included two-dimensional coordinate spaces (e.g., two-dimensional common coordinate space, two-dimensional actual coordinate space 520, two-dimensional virtual coordinate space 530). In some embodiments, registration can include registration having three-dimensional coordinate spaces, or any other number of dimensions.

As described, the image-guided surgical navigation system 110 may be used by the medical professional 102 (FIG. 1) for aiding the medical professional 102 during a medical procedure. The image-guided surgical navigation system 110 may utilize information from a preoperative image, such as a three-dimensional MRI image, for guiding the medical professional 102 during the medical procedure. For example, the three-dimensional MRI image may depict several fiducial markers affixed to an area of interest or one or more landmark features. During the medical procedure, the image-guided surgical navigation system 110 may correlate intraoperative images captured by an imaging device 122 or a wide-field camera 130 (FIG. 1) with the preoperative three-dimensional MRI image. Because the preoperative three-dimensional image may provide three-dimensional position information associated with the fiducial markers or landmark features, the intraoperative image captured by the imaging device 122 or the wide-field camera 130 may need to provide three-dimensional position information associated with the same fiducial markers or landmark features.

To provide three-dimensional position information, an intraoperative imaging device may be a CT, MRI, ultrasound, OCT, or three-dimensional scanning device. Because such intraoperative imaging devices for providing three-dimensional position information may require complex setup, and because it may not be feasible to utilize such intraoperative imaging devices in a common operating room environment 100, as will be described, it may be useful to leverage existing two-dimensional image capturing devices for capturing two-dimensional intraoperative images and generating depth information from the captured two-dimensional intraoperative images.

Further, in some scenarios, once reference markers have been affixed to the patient's anatomy, reference markers may inadvertently shift or be displaced from its original preoperative position. For example, during the medical procedure, one or more reference markers may be inadvertently bumped or shifted, thereby causing error in existing registration of the preoperative image. Accordingly, as will be described, it may be useful for image-guided surgical navigation systems to identify and correct for such registration error caused, for example, by inadvertent shifts of reference markers or landmark features after preoperative images have been registered in the common coordinate space. That is, a method of updating an existing landmark registration of one or more landmark features may be desirable.

Figure 6:
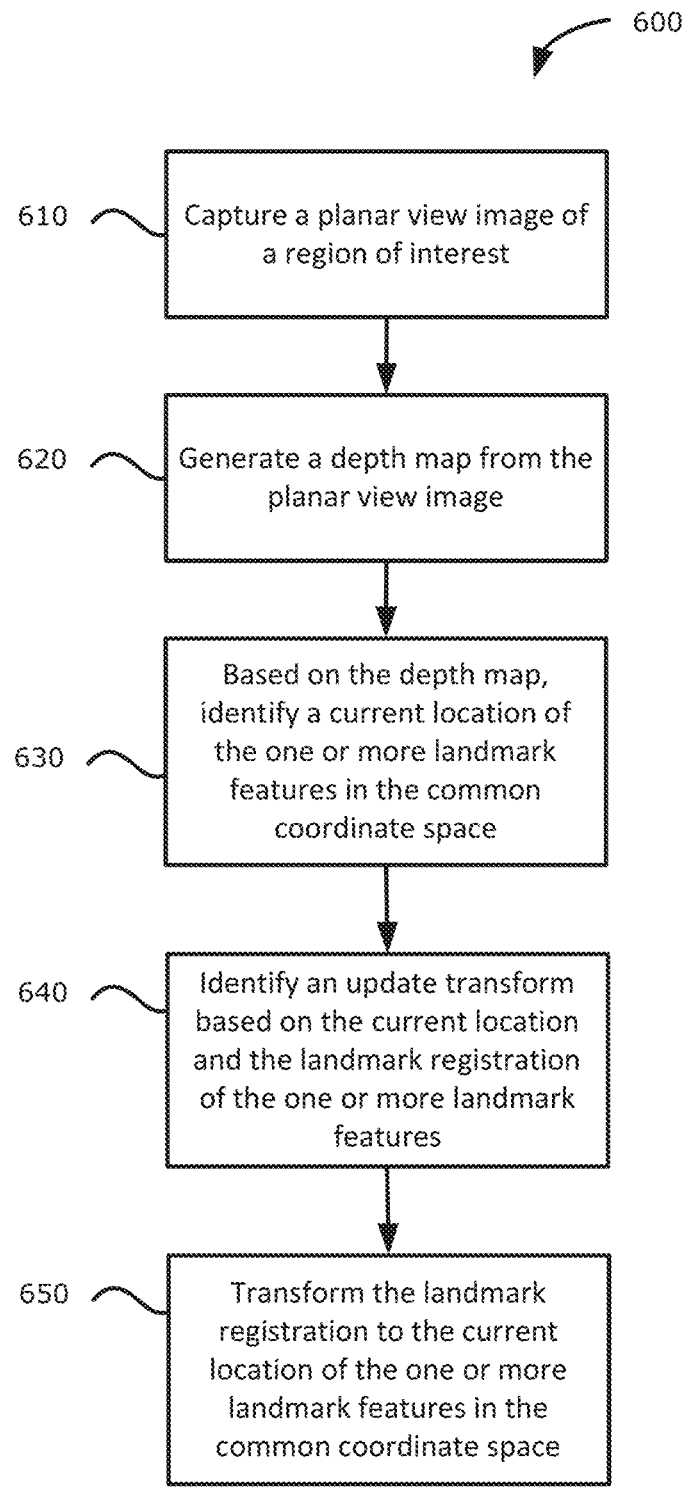
FIG. 6 illustrates, in flowchart form, a method of updating an existing landmark registration of one or more landmark features in a common coordinate space of the image-guided surgical navigation system of FIG. 1, in accordance with an embodiment of the present application.

Reference is now made FIG. 6, which illustrates, in flowchart form, a method 600 of updating an existing landmark registration of one or more landmark features in a common coordinate space of the image-guided surgical navigation system 110 (FIG. 1), in accordance with an embodiment of the present application. The method 600 may include operations that may be carried out by the image-guided surgical navigation system 110. The method 600 may be implemented, at least in part, through processor-executable instructions stored for example at the data storage device 342 (FIG. 3). For example, the processor-executable instructions may be executed by the processor 302 (FIG. 3). In some examples, one or more of the operations may be implemented via processor-executable instructions in the memory 304 (FIG. 3) or other data storage devices.

To illustrate the method 600 of FIG. 6, simultaneous reference will be made to FIG. 7, which illustrates a planar view image 700 of a region of interest 710, in accordance with an embodiment of the present application. The planar view image 700 may be captured, for example, by an imaging device 122 (FIG. 1). For the purposes of illustrating the method 600 of FIG. 6, the planar view image 700 may be captured during an exemplary craniotomy procedure, where the medical professional 102 (FIG. 1) may be performing a tumor resection procedure. The imaging device 122 may capture intraoperative images of the region of interest 710, and the planar view image 700 may be a two-dimensional image.

As described, the image-guided surgical navigation system 110 (FIG. 1) may be configured to correlate coordinate spaces through registration, such that data positioned in one coordinate space may be mapped to another coordinate space. Accordingly, the image-guided surgical navigation system 110 may correlate: (1) a physical location of a landmark feature on the patient in an actual coordinate space (e.g., intraoperative image) to (2) a location of that landmark feature on the patient in the virtual coordinate space (e.g., preoperative image, where that landmark reference is associated with a virtual representation of the patient). In some examples, the landmark feature may be fiducial markers affixed to the patient's anatomy (e.g., brain tissue) during capture of preoperative images. In other examples, the landmark feature may be uniquely identifiable structures or features, such as readily identifiable indentations or contours in tissue. Referring to FIG. 7, an example landmark feature may include a unique arrangement of crevices 716 of the brain tissue of the patient. As will be illustrated, the image-guided surgical navigation system 110 (FIG. 1) may evaluate the location of that landmark feature based on intraoperative images for updating the existing landmark registration.

At operation 610, the processor 302 (FIG. 3) of the image-guided surgical navigation system 110 may capture the planar view image 700 of the region of interest 710. The planar view image 700 may include illustration of one or more landmark features. In FIG. 7, one or more landmark features may include identifiable portions of the patient's anatomy, such as a uniquely identifiable (or uniquely arranged cluster of) blood vessel(s), or a distinguishable structure, such as a readily identifiable indentation or contour in tissue characterized by a rapid change in depth or elevation.

In some embodiments, the one or more landmark features may include fiducial reference markers, tantalum beads, cranio-maxofacial screws, or reflective markers (not illustrated in FIG. 7) affixed to portions of the patient's anatomy.

As described, although preoperative images may be captured using three-dimensional imaging devices, such as MRI, CT, OCT, or 3D scanner devices, it may be infeasible to operate such three-dimensional imaging devices within the operating room environment 100 (FIG. 1). Accordingly, at operation 610, the planar view image 700 of the region of interest 710 may be captured using existing two-dimensional image capturing devices. The planar view image 700 may generally be a two-dimensional image of the region of interest 710.

In some embodiments, the image-guided surgical navigation system 110 may be configured to project an edge indicator onto the region of interest 710. In an example, the projection device 328 (FIG. 3) may be used for projecting the edge indicator onto the region of interest 710. The edge indicator may include grid-like projections of light in the form of horizontal lines 712 and/or vertical lines 714. The horizontal lines 712 may be projected substantially perpendicular to the vertical lines 714. The horizontal lines and the vertical lines may be projected onto the region of interest 710, and the respective projection of light may appear to conform to the contour of the surface illustrated within the area of interest 710. Accordingly, the projected horizontal lines 712 may not appear to be perpendicular to the projected vertical lines 714, as the projections may appear to conform to any contours of the surface (e.g., tissues) in the region of interest 710.

While a grid-like pattern may be illustrated, other arrangement of lines or indicators may be projected within the region of interest 710 for assisting identification of landmark features. As will be described in an example herein, the projected edge indicator may assist whilst generating a depth map from the planar view image 700. For example, generating the depth map may include determining image sharpness of the one or more landmark features. In some scenarios, the one or more landmark features may not be easily distinguishable. That is, an example landmark feature may not exhibit sharp edges sufficient to distinguish that example landmark feature from an adjacent landmark feature. As a result, the projected edge indicator may provide additional visual features in the planar view image 700 that may be captured and analyzed by the imaging device 122.

Figure 7:
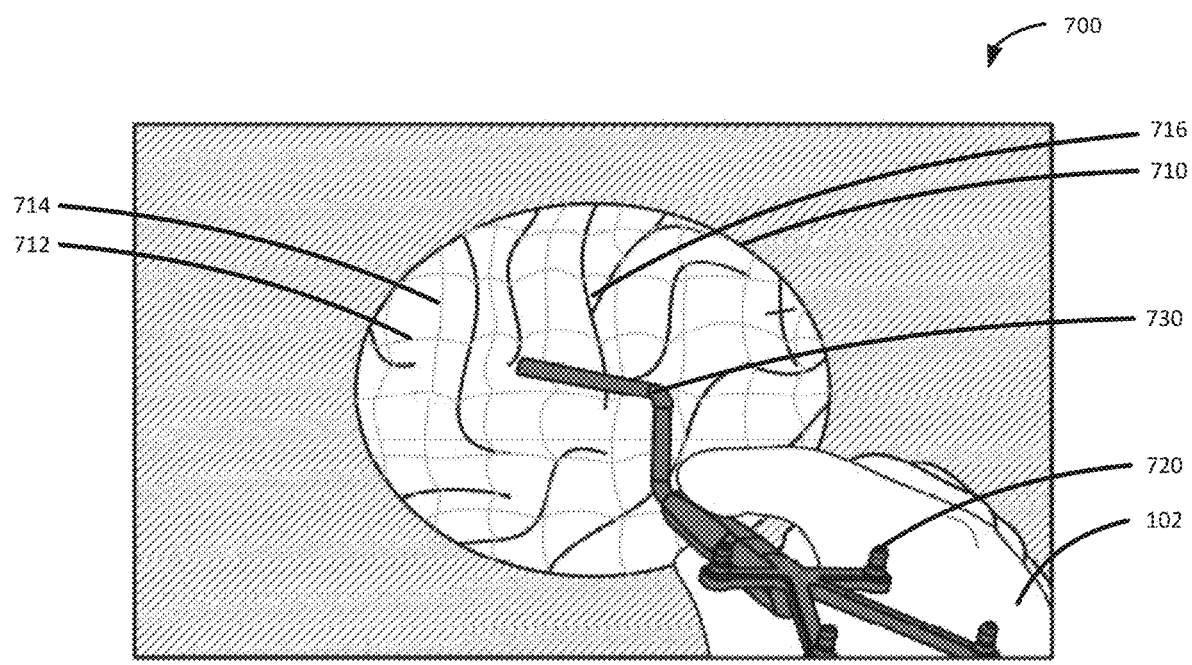
FIG. 7 illustrates a planar view image of a region of interest, in accordance with an embodiment of the present application.

Referring still to FIG. 7, the planar view image 700 may include an illustration of a surgical instrument 730 manipulated by the medical professional 102 (FIG. 1) during the medial procedure. The surgical instrument 730 may include a series of fiducial markers 720 attached thereto. The series of fiducial markers 720 may be detectable by the tracking detector 114 (FIG. 1) and/or captured in intraoperative images generated by the imaging device 122 (FIG. 1) during the medical procedure. In some examples, the surgical instrument 730 may be required for touch point identification of the one or more landmark features.

Referring again to FIG. 6, at operation 620, the processor 302 may generate a depth map from the planar view image 700. Because it may be infeasible to operate the same preoperative three-dimensional imaging device within the operating room environment 100, the processor 302 may generate the depth map from the planar view image 700 for correlating any preoperative image with an intraoperative image captured by the imaging device 122.

Continuing with the example with reference to FIG. 7, the processor 302 may generate the depth map based on touch point identification of the one or more landmark features. As the planar view image 700 may be a two-dimensional image, the planar view image 700 alone, without further analysis, may not provide spatial angle and orientation information of the one or more landmark features in the common coordinate space (e.g., a three-dimensional coordinate space) of the image-guided surgical navigation system 110. Overall, the imaging device 122 may capture a state of the fiducial markers 720 when a "touch" is made on the landmark feature, and the processor 302 may determine spatial angle and orientation of the landmark feature based on the state of the fiducial markers 720 at that "touch". Thus, depth information may be associated with the spatial angle and orientation associated with the landmark feature at that "touch". In some examples, capturing the state of the fiducial markers 720 may involve a combination the imaging device 122 and the tracking detector 114 capturing the state of the fiducial markers 720 at that "touch".

A depth-of-field (DOF) may be a distance between the nearest and furthest objects in a camera's field-of-view that appear to be in focus for the planar view image 700. In some embodiments, the DOF and the midpoint between the "near" and "far" edges (e.g., working distance) may be controlled by optical elements in the imaging device 122 (FIG. 1). By determining portions of a captured image that may be in focus, distance or depth information from those portions may be extracted or calculated. That is, by changing the working distance and analyzing the change in focus of portions of the planar view image 700, the depth map of the region of interest 710 may be generated. In some examples, narrowing a depth-of-field may increase resolution in depth determination.

Thus, in some embodiments, the depth map may be generated based on contrast sweep image data or focus sweep image data of the imaging device 122 (FIG. 1). For example, at operation 620, the processor 302 may configure the imaging device 122 to perform a focus sweep for capturing a plurality of intraoperative images such that substantially all of the one or more landmark features of the region of interest 710 may be in focus in at least one of the plurality of intraoperative images. That is, the planar view image 700 may include a plurality of intraoperative images, and the plurality of intraoperative images may be stored in the data storage device 342 (FIG. 1) and, subsequently, may be analyzed for generating the depth map.

The depth map may be generated based on the planar view image 700, or the plurality of intraoperative images captured by the imaging device 122. The processor 302 may be configured to determine image sharpness of each of the one or more landmark features within each of the plurality of intraoperative images and identify depth data based on the focus depth of each of the plurality of intraoperative images. For example, the processor 302 may be configured to determine visual sharpness of intersecting horizontal lines 712 and vertical lines 714 in the grid-like pattern. The determined visual sharpness of intersecting lines may be a proxy for determining whether the particular area surrounding the intersecting lines may be in focus. In another example, the processor 302 may generate the depth map based on determining polarization of light reflected from particular areas of the region of interest 710.

In some examples, the one or more landmark features within the region of interest 710 may be readily identifiable and may exhibit sufficient edge contrast, such that the processor 302 may determine the sharpness of each of the one or more landmark features without the projected edge indicator. For example, referring again to FIG. 7, the unique arrangement of crevices 716 may exhibit readily identifiable contours characterized by sharp changes in depth or elevation. Accordingly, the processor 302 may be able to determine, based on the successive intraoperative images, the focus depth that provides the sharpest image of the unique arrangement of crevices 716.

In the present example, the planar view image 700 may include the plurality of intraoperative images. As each of the plurality of intraoperative images may be associated with a focus depth, and as the processor 302 may be configured to determine in which of the plurality of intraoperative images a landmark feature may exhibit the greatest visual sharpness (as compared to other intraoperative images in the plurality of intraoperative images), the processor 302 may determine depth map information for each of the one or more landmark features.

Based on the depth map, at operation 630, the processor 302 identifies a current location of the one or more landmark features in the common coordinate space. For example, based on the depth map information, the processor 302 may determine spatial angle and orientation information for each of the one or more landmark features for determining the current location of the one or more landmark features in the common coordinate space.

For example, the one or more landmark features may exist in the actual coordinate space 520 (FIG. 5). Using registration process operations (e.g., operations described with reference to FIG. 5), the processor 302 may import coordinates from the actual coordinate space 520 to the virtual coordinate space 530 (FIG. 5) for correlating the current location of the one or more landmark features with the location of the one or more landmark features in the preoperative image.

In some scenarios, the one or more landmark features may inadvertently have shifted or been displaced from an original position identified in a preoperative image. At operation 640, the processor 302 may identify an update transform based on the current location and the existing landmark registration of the one or more landmark features for updating the existing landmark registration. For example, the current location of the one or more landmark features may be based on the generated depth map (e.g., from operation 630), while the existing landmark registration of the one or more landmark features may be based on registration of the previously acquired preoperative image in the common coordinate space. Because the current location and the existing landmark registration may differ for landmark features that may have inadvertently shifted or displaced, the identified update transform may represent the difference between: (1) the previously determined landmark registration from the preoperative image; and (2) the current location of the one or more landmark features based on the planar view image 700.

At operation 650, the processor 302 may transform the existing landmark registration of the one or more landmark features to the current location of the one or more landmark features in the common coordinate space. Accordingly, the existing landmark registration of the one or more landmark features may be updated to account for inadvertent displacement or shifts from the original position of the one or more landmark features identified in the previously acquired preoperative image. In the examples described herein, an existing landmark registration may include one or landmark features; however, the existing landmark registration of some embodiments described herein can also include features of surface trace registration, features of rapid registration, or other example features of patient registration for the image-guided surgical navigation system.

In some embodiments, the processor 302 may be configured to overlay the depth map (e.g., from operation 620) on an existing registration image of the one or more landmark features in the common coordinate space. The existing registration image may illustrate the virtual representation of the one or more landmark features in the common coordinate space, where the virtual representation may be based on the preoperative image.

Figure 8A:
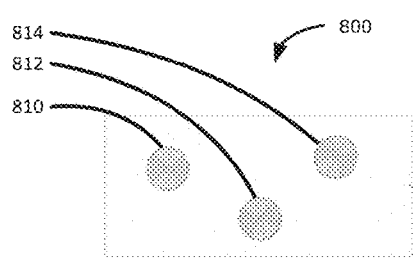
FIGS. 8A, 8B, and 8C illustrate a series of intraoperative planar view images, in accordance with embodiments of the present application.

To illustrate, reference will now be made to FIGS. 8A, 8B, and 8C, which illustrate a series of intraoperative planar view images, in accordance with an embodiment of the present application. FIG. 8A depicts an example intraoperative planar view image 800 illustrating a first landmark feature 810, a second landmark feature 812, and a third landmark feature 814, in accordance with an embodiment of the present application. The intraoperative planar view image may be based on images captured by the imaging device 122 (FIG. 1) during the medical procedure.

Figure 8B:
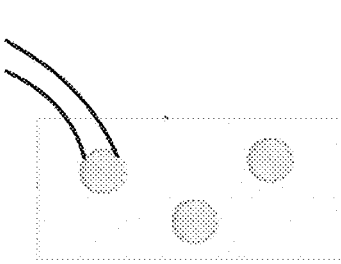

FIG. 8B depicts an overlaid image, where the overlaid image includes an overlay of an existing registration image on the intraoperative planar view image 800 of FIG. 8A in the common coordinate space. As described, the existing registration image may illustrate a virtual representation of the first landmark feature 810, the second landmark feature 812, and the third landmark feature 814 based on a preoperative image. In FIG. 8B, for ease of exposition, the first landmark feature 810 is identified, and the second landmark feature and the third landmark feature is not numerically identified.

The overlay representing the first landmark feature 810 appears to substantially correspond to a virtual representation of the first landmark feature in the common coordinate space. As the overlay depicting the current location of the landmark feature substantially overlays the virtual representation in the common coordinate space (e.g., virtual representation based on registration of preoperative image), the update transform identified at operation 640 may represent an insignificant difference between: (1) the previously determined landmark registration from the preoperative image; and (2) the current location of the one or more landmark features based on the intraoperative planar view image. Overall, FIG. 8B illustrates that the respective landmark features (e.g., the first landmark feature, the second landmark feature, and the third landmark feature) have not been inadvertently shifted or displaced from the original landmark feature locations, thereby indicating good registration of the one or more landmark features.

Figure 8C:
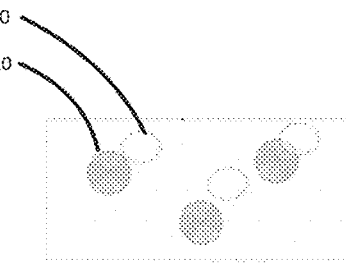

In contrast to FIG. 8B, FIG. 8C depicts an overlay of the existing registration image on the intraoperative planar view image 800 in the common coordinate space. In FIG. 8C, the virtual representation 820 (e.g., from the existing registration image) of the first landmark feature appears to be shifted relative to the overlay representing the first landmark feature 810 from the depth map obtained at operation 620. As the overlay depicting the current location of the landmark features (e.g., based on the intraoperative planar view image 800) appears to differ from the virtual representation of the landmark features, the update transform identified at operation 640 may represent the displacement from: (1) the previously determined landmark registration from the preoperative image; to (2) the current location of the one or more landmark features based on the intraoperative planar view image. Based on the overlay of the depth map and the existing registration image illustrated in FIG. 8C, the processor 302 may readily identify that the existing landmark registration may be erroneous, and that the erroneous landmark registration may have been caused by an inadvertent bump or shift of the landmark features from the original locations. In FIG. 8C, each of the first landmark feature 810, the second landmark feature 812, and the third landmark feature 814 may inadvertently have been displaced by substantially the same distance. However, in some examples, each of the one or more landmark features may inadvertently be displaced by a substantially different distance, as compared to another of the one or more landmark features.

In some embodiments, the processor 302 may be configured to display, on the display 116 (FIG. 1), the overlay of the existing registration image on the generated depth map (e.g., from operation 620) for visually illustrating to the medical professional 102 the discrepancies in position of the one or more landmark features in the existing registration image and the depth map.

Referring again to FIG. 8B, the respective landmark features may not have shifted or been displaced from the original landmark feature locations. Thus, any update transform identified at operation 640 for the scenario depicted in FIG. 8B may result in an insignificant update to the existing landmark registration of the respective landmark features. Accordingly, in some embodiments, the processor 302 may determine whether the determined update transform (e.g., determined at operation 640) may shift the existing landmark registration beyond a threshold position limit. For example, the threshold position limit may be a distance related threshold limit. That is, if any of the location coordinates of the landmark features would be shifted by more than 3 distance units in the common coordinate space, the processor 302 may determine that the update transform shifts the existing landmark registration beyond the threshold position limit. In the scenario depicted in FIG. 8B, because the landmark features appear to substantially correspond to the current location of the respective landmark features, the processor 302 may determine that the update transform may not shift the existing landmark registration beyond the threshold position limit. The processor 302 may not apply the update transform to the existing landmark registration. That is, the processor 302 may determine that the existing landmark registration need not be updated.

In contrast, in FIG. 8C, the respective landmark features may have inadvertently shifted or have been displaced from the original landmark feature locations. In the scenario illustrated in FIG. 8C, the processor 302 may determine that the update transform (e.g., determined at operation 640) may shift one or more of the location coordinates of the landmark features by more than 3 distance units in the common coordinate space. The processor 302 may determine that the update transform shifts the existing landmark registration beyond the threshold position limit. Accordingly, the processor 302 may transform the existing landmark registration to the current location of the one or more landmark features in the common coordinate space. Although the above example describes the threshold position limit in terms of distance units, in some embodiments, the threshold position limit may be defined with other units, such as degrees of rotation, etc.

Referring again to FIG. 6, the processor 302 may be configured to generate the depth map from the planar view image 700 (FIG. 7) based on other techniques. In some embodiments, the imaging device 122 (FIG. 1) may be a stereoscopic imaging device, and the processor 302 may generate the depth map based on planar view images captured by the stereoscopic imaging device.

For example, the stereoscopic imaging device may include a first camera and a second camera adjacent the first camera. The first camera and the second camera may be oriented in a similar direction, and images captured by the first camera and the second camera may be configured to simulate binocular vision for capturing three-dimensional images and for providing depth information. That is, the planar view image 700 (FIG. 7) may include a set of images from the first camera and the second camera.

In some embodiments, the processor 302 may generate the depth map based on touch point identification of the one or more landmark features. For example, the image-guided surgical navigation system 110 may be configured to identify, via detection of the fiducial markers 720 (FIG. 7), the location of the surgical instrument 730 (FIG. 7). When the medical professional 102 utilizes the surgical instrument 730 for "touching" the one or more landmark features, the identified location in the common coordinate space of the surgical instrument 730 (FIG. 7) at the respective landmark features may be associated with spatial angle and orientation information relating to the surgical instrument. The spatial angle and orientation information may be correlated with depth information for that respective landmark feature. Accordingly, based on the series of touch point identification of the one or more landmark features, the processor 302 may be configured to generate the depth map from the planar view image 700 captured intraoperatively.

In some embodiments, the processor 302 may generate the depth map based, in part, on identifying the one or more landmark features using at least one of a scale invariant feature transform (SIFT) or a speeded up robust features (SURF) algorithm.

As described, the imaging device 122 may be positioned to capture planar view images in the operating room environment 100. In some scenarios, however, the imaging device 122 may be inadvertently be positioned such that no landmark features may be within a field of view of the imaging device 122. In some scenarios, landmark features may not be within the field of view because the field of view may include a portion of the patient's anatomy without readily identifiable contours in tissues nor uniquely identifiable anatomical features (e.g., uniquely arranged cluster of blood vessels or tissue mass). In some scenarios, landmark features may not be within the field of view because the field of view may be associated with a zoomed in view (e.g., long focal range setting associated with the imaging device 122), and the one or more landmark features may be outside the field of view. Accordingly, it may be useful to identify whether at least one of the one or more landmark features may be identified in the region of interest 710 (FIG. 7) prior to capturing the planar view image 700 of the region of interest 710.

Thus, in some embodiments, prior to capturing the planar view image 700 of the region of interest 710, the processor 302 may be configured to determine that at least one of the one or more landmark features may be identified within the region of interest 710.

When the processor 302 determines that at least one of the one or more landmark features is not identified within the region of interest 710, the processor 302 may be configured to increase the field of view of the imaging device 122 to identify at least one of the one or more landmark features. Accordingly, positively identifying at least one of the one or more landmark features prior to capturing the planar view image 700 may provide assurance that the planar view image 700 may be useful for operations relating to updating the existing landmark registration in the common coordinate space of the image-guided surgical navigation system 110.

Certain adaptations and modifications of the described embodiments can be made. Therefore, the above discussed embodiments are considered to be illustrative and not restrictive.

What is claimed is:

1. A method of updating an existing landmark registration in a three-dimensional coordinate space of one or more landmark features of anatomy being imaged by an image-guided surgical navigation system, the method comprising:
   capturing a planar view image of a region of interest, the planar view image being a two-dimensional image of the one or more landmark features;
   generating a depth map from the planar view image captured by a stereoscopic imaging device, wherein generating the depth map includes determining depth data using identified visual characteristics of the one or more landmark features, wherein the one or more landmark features includes an identifiable portion of the anatomy in the planar view image, wherein generating the depth map includes generating the depth map based on touch point identification of the one or more landmark features;
   based on the depth map, identifying a current location of the one or more landmark features in the three-dimensional coordinate space; and
   transforming the existing landmark registration to the current location of the one or more landmark features in the three-dimensional coordinate space.

2. The method of claim 1, wherein generating the depth map includes generating the depth map based on at least one of focus sweep or contrast sweep image data of the one or more landmark features.

3. The method of claim 1, wherein the one or more landmark features include at least one of fiducial markers, tantalum beads, cranio-maxofacial screws, reflective markers, or distinguishing object features.

4. The method of claim 1, wherein transforming the existing landmark registration to the current location of the one or more landmark features in the three-dimensional coordinate space includes:
   identifying an update transform based on the current location and the existing landmark registration of the one or more landmark features for updating the existing landmark registration of the one or more landmark features;
determining whether the update transform shifts the existing landmark registration beyond a threshold position limit; and
when the update transform shifts the existing landmark registration beyond the threshold position limit, transforming the existing landmark registration to the current location of the one or more landmark features in the three-dimensional coordinate space.

5. The method of claim 1, wherein generating the depth map includes identifying the one or more landmark features using at least one of a scale invariant feature transform (SIFT) or a speeded up robust features (SURF) algorithm.

6. The method of claim 1, further comprising:
prior to capturing the planar view image of the region of interest, determining that at least one of the one or more landmark features is identified within the region of interest; and
when at least one of the one or more landmark features is not identified within the region of interest, increasing a field of view to identify at least one of the one or more landmark features.

7. The method of claim 1, further comprising:
overlaying the depth map of the planar view image on an existing registration image of the one or more landmark features in the three-dimensional coordinate space; and
displaying an overlaid image for visually illustrating discrepancies between the existing registration image and the depth map of the one or more landmark features.

8. The method of claim 1, wherein generating the depth map includes:
determining image sharpness of one or more landmark features from a plurality of intraoperative images obtained by performing a focus sweep of the anatomy being imaged; and
identifying depth data based on the determined image sharpness of the one or more landmark features in the plurality of intraoperative images.

9. An image-guided surgical navigation system, the system comprising:
a processor;
an imaging device coupled to the processor; and
a memory coupled to the processor and storing processor-readable instructions that, when executed, cause the processor to:
capture a planar view image of a region of interest, the planar view image being a two-dimensional image of one or more landmark features of anatomy being imaged by the imaging device;
generate a depth map from the planar view image captured by a stereoscopic imaging device, wherein generating the depth map includes determining depth data using identified visual characteristics of the one or more landmark features, wherein the one or more landmark features includes an identifiable portion of the anatomy in the planar view image, wherein generating the depth map includes generating the depth map based on touch point identification of the one or more landmark features;
based on the depth map, identify a current location of the one or more landmark features in a three-dimensional coordinate space; and
transform an existing landmark registration to the current location of the one or more landmark features in the three-dimensional coordinate space.

10. The image-guided navigation system of claim 9, wherein the processor-readable instructions that, when executed, cause the processor to generate the depth map from the planar view image includes:
generating the depth map based on at least one of focus sweep or contrast sweep image data of the one or more landmark features.

11. The image-guided navigation system of claim 9, wherein the one or more landmark features includes at least one of fiducial markers, tantalum beads, cranio-maxofacial screws, reflective markers, or distinguishing object features.

12. The image-guided navigation system of claim 9, wherein the processor-readable instructions that, when executed, cause the processor to transform the existing landmark registration to the current location of the one or more landmark features in the three-dimensional coordinate space includes:
identifying an update transform based on the current location and the existing landmark registration of the one or more landmark features for updating the existing landmark registration of the one or more landmark features;
determining whether the update transform shifts the existing landmark registration beyond a threshold position limit; and
when the update transform shifts the existing landmark registration beyond the threshold position limit, transforming the existing landmark registration to the current location of the one or more landmark features in the three-dimensional coordinate space.

13. The image-guided navigation system of claim 9, wherein the processor-readable instructions, when executed, further cause the processor to:
prior to capturing the planar view image of the region of interest, determine that at least one of the one or more landmark features is identified within the region of interest; and
when at least one of the one or more landmark features is not identified within the region of interest, increase a field of view to identify at least one of the one or more landmark features.

14. The image-guided navigation system of claim 9, wherein the processor-readable instructions, when executed, further cause the processor to:
overlay the depth map of the planar view image on an existing registration image of the one or more landmark features in the three-dimensional coordinate space; and
display an overlaid image for visually illustrating discrepancies between the existing registration image and the depth map of the one or more landmark features.

15. A non-transitory computer-readable storage medium comprising processor-executable instructions which, when executed, configure a processor to:
capture a planar view image of a region of interest, the planar view image being a two-dimensional image of the one or more landmark features of anatomy being imaged by an image-guided surgical navigation system;
generate a depth map from the planar view image captured by a stereoscopic imaging device, wherein to generate the depth map includes determining depth data using identified visual characteristics of the one or more landmark features, wherein the one or more landmark features includes an identifiable portion of the anatomy in the planar view image, wherein to generate the depth map includes generating the depth map based on touch point identification of the one or more landmark features;
based on the depth map, identify a current location of the one or more landmark features in a three-dimensional coordinate space; and
transform an existing landmark registration to the current location of the one or more landmark features in a three-dimensional coordinate space.

* * * * *